(12) United States Patent
Durr

(10) Patent No.: US 9,376,660 B2
(45) Date of Patent: Jun. 28, 2016

(54) METHOD FOR INCREASING THE COQ10 AND COQH2 CONTENT IN PHOTOTROPHIC MICROORGANISMS

(75) Inventor: Oliver Durr, Baar (CH)

(73) Assignee: Sanbo International Establishment (LI)

(\*) Notice: Subject to any disclaimer, the term of this patent is extended or adjusted under 35 U.S.C. 154(b) by 0 days.

(21) Appl. No.: 13/994,805

(22) PCT Filed: Dec. 21, 2011

(86) PCT No.: PCT/EP2011/073594
§ 371 (c)(1),
(2), (4) Date: Sep. 12, 2013

(87) PCT Pub. No.: WO2012/085086
PCT Pub. Date: Jun. 28, 2012

(65) Prior Publication Data
US 2014/0295530 A1    Oct. 2, 2014

(30) Foreign Application Priority Data
Dec. 21, 2010  (EP) ................................. 10196124

(51) Int. Cl.
| C12P 7/66 | (2006.01) |
| C12N 1/38 | (2006.01) |
| C12N 1/20 | (2006.01) |
| C12N 1/12 | (2006.01) |
| A23D 9/00 | (2006.01) |
| C11B 1/10 | (2006.01) |
| C11C 1/00 | (2006.01) |

(52) U.S. Cl.
CPC .. C12N 1/38 (2013.01); C12N 1/12 (2013.01); C12N 1/20 (2013.01); C12P 7/66 (2013.01); A23D 9/00 (2013.01); C11B 1/10 (2013.01); C11C 1/002 (2013.01); C12N 2500/24 (2013.01); C12N 2529/10 (2013.01)

(58) Field of Classification Search
None
See application file for complete search history.

(56) References Cited

U.S. PATENT DOCUMENTS

| 6,395,521 B1 * | 5/2002 | Miura ........................... 435/168 |
| 2003/0017558 A1 * | 1/2003 | Pham et al. ................... 435/134 |
| 2011/0014663 A1 | 1/2011 | Suzuki et al. |
| 2011/0030097 A1 * | 2/2011 | Maor et al. .................... 800/281 |

FOREIGN PATENT DOCUMENTS

| JP | 2001-061466 A | 3/2001 |
| JP | 2007-089580 A | 4/2007 |
| JP | 2009-179587 A | 8/2009 |
| JP | 2010-530241 A | 9/2010 |
| JP | 2010-246473 A | 11/2010 |
| WO | 2008155781 A2 | 12/2008 |
| WO | WO 2009/055951 | 5/2009 |
| WO | 2009093703 A1 | 7/2009 |
| WO | WO 2010020989 A1 * | 2/2010 |

OTHER PUBLICATIONS

Pulz "Photobioreactors: production systems for phototrophic microorganisms", Applied Microbiology and Biotechnology 57: 287-293, 2001.*
Machine-generated Translation of Buccholz (WO 2009/055951) published May 7, 2009.*
Siedow, JN et al. Plant mitochondrial electron transfer and molecular biology. The Plant Cell. 1995. 7: 821-831.*
Pinto, E et al. Heavy metal-induced oxidative stress in algae. Journal of Phycology. 2003. 39: 1008-1018.*
Szivak, I et al. Metal-induced reactive oxygen species production in Chlamydomonas reinhardtii (Chlorophyceae). Journal of Phycology. 2009. 45: 427-435.*
Kosourov, SN et al. A truncated antenna mutant of Chlamydomonas reinhardtii can produce more hydrogen than the parental strain. International Journal of Hydrogen Energy. 2011. 36: 2044-2048. Available online on Nov. 30, 2010.*
Mojaat, M., Pruvost, J., Foucault, A., Legrand, J., 2007, Effect of organic carbon sources and Fe2+ ions on growth and β-carotene accumulation by Dunaliella salina, Biochemical Engineering Journal, p. 177-184.
Shcolnick, S., Summerfield, T.C., Reytman, L., Sherman, L.A., and Keren, N., 2009, The Mechanism of Iron Homeostasis in the Unicellular Cyanobacterium *Synechocystis* sp. PCC 6803 and Its Relationship to Oxidative Stress, American Society of Plant Biologists, p. 2045-2056.
Yoshida, H., Kotani, Y., Ochiai, K., and Araki, K., 1998, Production of ubiquinone-10 using bacteria, J. Gen. Appl. Microbiol., p. 19-26.
Korenaga, M., et al., 2010, Iron Inducted Oxidative Stress Inhibits Viral Replication in Full Genomic Hepatitis C Virus Replicon Cells, Hepatology, AASLD Abstracts.
Enzmann, F.H., 2012, Ubiquinon/ol Q10—der Schlüssel zur Mitochondrialen Medizin, Om—Zs. F. Orthomol. Med., p. 17-19.

(Continued)

*Primary Examiner* — Renee Claytor
*Assistant Examiner* — Susan E Fernandez
(74) *Attorney, Agent, or Firm* — George Pappas

(57) ABSTRACT

A method for increasing the content of ubiquinone (CoQ10) and ubiquinol (CoQH2) in phototrophic microorganisms that were cultivated in a culture medium in a bioreactor under light irradiation, wherein the phototrophic microorganisms are selected from the group consisting of blue algae, green algae and yellow-green algae, comprising a step of inducing oxidative stress. By virtue of the fact that oxidative stress was induced by incubating the phototrophic microorganisms together with $Fe^{3+}$ in the culture medium, a higher content of CoQ10 and CoQH2 is obtained. Moreover, the microorganisms thus obtained have a higher content of trivalent iron, which is particularly relevant for the human diet. From the phototrophic microorganisms it is possible to produce an oily extract and also a dried algae product.

3 Claims, No Drawings

(56) References Cited

OTHER PUBLICATIONS

Morré, D.F., Guo, F., and Morré, D.J., 2003, An aging-related cell surface NADH oxidase (arNOX) generates superoxide and is inhibited by coenzyme Q, Molecular and Cellular Biochemistry 254, p. 101-109.

Jones, R.F., Speer, H.L., and Kury, W., 1963, Studies on the Growth of the Red Alga Porphyridium cruentum, Physiologia Plantarum, vol. 16, p. 636-643.

* cited by examiner

METHOD FOR INCREASING THE COQ10 AND COQH2 CONTENT IN PHOTOTROPHIC MICROORGANISMS

This application claims priority from PCT Application No. PCT/EP2011/073594 filed Dec. 21, 2011 which claims priority from European Application No. EP 10196124.1 filed on Dec. 21, 2010, which applications are incorporated herein by reference.

TECHNICAL FIELD

The invention relates to a method for increasing the CoQ10 and CoQH2 content in phototrophic microorganisms.

BACKGROUND OF THE INVENTION

Ubiquinone (2,3-dimethoxy-5-methyl-6-multiprenyl-1,4-benzoquinone, $C_{59}H_{90}O_4$, 863.34 g/mol), also known as Co-Enzyme$Q_{10}$ or shortly CoQ10, is of particular importance for nearly all living cells due to its antioxidative properties. CoQ10 is present in most aerobic microorganisms and in all animals, and CoQ10 is essential also for the human organism.

In the unstressed human organism, the reduced form of CoQ10, namely ubiquinol (2,3-dimethoxy-5-methyl-6-multiprenyl-1,4-hydroquinone, $C_{59}H_{92}O_4$, 865.36 g/mol), also called CoQH2, is predominant.

Ubiquinol accounts for more than 80% of the total CoQ10 content in the human plasma and is thus an important plasma antioxidant for lipoproteins. Ubiquinol inhibits the oxidation of proteins and lipids in cell membranes and protects against lipid peroxidation and oxidative DNA degeneration, but also against other harmful molecules. Oxidative stress of all types, in particular caused by inflammation, can results in cell death. In his treatise "Schlüssel zur Mitochondrialen Medizin" F. H. Enzmann has indicated that the proportion of the oxidized form of CoQ10 to the reduced form of CoQH2 is 10:90. According to other authors, this ratio can vary between 10:30 and 10:90.

Morré and Morré (Morré, D. M., Guo, F. and Morré, D. J. An aging-related cell surface NADH oxidase (arNOX) generates superoxide and is inhibited by coenzyme CoQ10. *Mol. Cell. Biochem.* 264:101-109) describe a special source of extracellular ROS that they called "age-related NADH oxidase" or "arNOX proteins". Studies have shown that ubiquinone (CoQ10) which is applied onto the skin penetrates into the layers of the epidermis where it reduces the oxidation degree and inhibits the arNOX activity, respectively. In contrast, CoQH2 and the molecules CoQ0, CoQ2, CoQ4, CoQ6, and CoQ7 showed no such effect. It could be shown that the inhibition can be attributed exclusively to the side chain of CoQ10 (n-decaprenol).

WO 2009/055951 describes a method for increasing the Co-Enzyme-Q10 content in phototrophic microorganisms that were cultivated in a culture medium in a bioreactor under standard conditions, with the growth of said microorganisms showing an exponential and a stationary growth phase. In said patent document, microalgae selected from the divisions Rhodophyta, Chlorophyta and Haptophyta, particularly *Porphyridium purpureum, Chlorella vulgaris, Pavlova lutheri* or *Cricosphaera carterae*, are mentioned as useful phototrophic microorganisms. The method described in WO 2009/055951 comprises as an essential step the induction of oxidative stress by co-incubation of stress-inducing substances and/or by increasing the surface radiation strength at the bioreactor. Alternatively or additionally, this can be achieved by adding oleate to the culture medium.

As an appropriate measure for inducting oxidative stress, it is proposed in WO 2009/055951 to carry out, particularly at the end of the exponential growth phase, a co-incubation of 13S-hydroperoxy-9Z,11 E-octadecadienoic acid and bivalent iron (Fe(II) and $Fe^{2+}$ respectively) with the microorganisms in the culture medium.

Considering the known advantageous effects of CoQ10, which are also described particularly in WO 2009/055951, there is still a clear need for further improvement of the methods for producing CoQ10 and CoQH2.

It is conceivable that a further increase of the CoQ10 and CoQH2 content could be achieved by means of genetically modified algae. However, the use of such microorganisms is not devoid of problems, and, moreover, the bioavailability and the efficacy of such an approach would first have to be determined under the present quality standards.

SUMMARY OF THE INVENTION

It is an object of the present invention to provide a method for providing CoQ10 and CoQH2 in commercially competitive way with a constant high quality and a high yield of natural material by means of genetically non-transformed organisms.

According to the method of the present invention, induction of oxidative stress is achieved by incubation of trivalent iron (for example in the form of $Fe^{3+}$) with green algae, blue algae and yellow-green algae, respectively in the culture medium.

Surprisingly, it was found that the addition of trivalent iron instead of the known addition of bivalent iron to the algae species mentioned above results in a higher yield of CoQ10.

A further object of the invention is to provide phototrophic microorganisms with an enhanced content of CoQ10.

The addition of $Fe^{3+}$ per liter of culture medium is advantageously about 1 mg/l to about 6 mg/l, in particular about 3 mgA to about 4 mg/l. In the case of blue algae, preferably about 2.7 mg/l and in the case of green and yellow-green algae preferably about 3.5 mgA $Fe^{3+}$ per liter of culture medium are incubated.

According to the invention, an incubation of trivalent iron (Fe(III) or $Fe^{3+}$) leads to an increased oxidative stress for the group of blue algae, green algae and yellow-green algae. Without being bound by theory, it is assumed that the substance triggers a lipid peroxidation which acts as an initial reaction step in membrane destruction. In response to this stress event, the algae react with an increased formation of antioxidative substances, particularly with an increased formation of CoQ10 and CoQH2.

As a result, iron remains present in the algae in an amount of 33 µg/g to 66 µg/g dry mass. This is an advantage particularly because the supply of iron-containing food is nowadays considered necessary.

Preferably, the phototrophic microorganisms have the following trivalent iron ($Fe^{3+}$) content by weight relative to the biomass:

for blue algae at least 10 µg/g;
for green algae and yellow-green algae at least 10 µg/g.

In an advantageous embodiment, the phototrophic microorganisms have the following trivalent iron ($Fe^{3+}$) content by weight relative to the biomass:

for blue algae at least 30 µg/g;
for green algae and yellow-green algae at least 60 µg/g.

DETAILED DESCRIPTION OF THE PREFERRED EMBODIMENTS

The mixotrophic growth of the microalgae is carried out in a photobioreactor through cultivation under the conditions previously determined for each species.

With regard to an increase of the CoQ10/CoQH2 formation in the microorganisms employed, an optimization of the surface radiation strength, but also the incubation of substances that induce an oxidative stress have a positive influence on the amount of extractable CoQ10 and CoQH2 in the biomass formed. This is caused, on the one hand, by an increased photooxidation due to the higher surface radiation strengths and, on the other hand, by a lipid peroxidation that is caused by the co-incubated substances increasing the oxidative stress.

Photooxidative stress in the microalgae only occurs above a defined radiation strength in the photobioreactor. However, the growth of the microorganisms cultivated in the bioreactor can substantially alter the optical density of the culture medium and, concomitantly, the light transmission at the bioreactor. In order to keep the photooxidative stress constant also under varying optical densities of the culture medium, the surface radiation strength $I_0$ at the bioreactor should advantageously be adapted as a function of light transmission. Preferably, this adaption of the surface radiation strength $I_0$ is made in the range between 40 $\mu E \cdot m^{-2} \cdot s^{-1}$ and 250 $\mu E \cdot m^{-2} \cdot s^{-1}$. This adaption of the surface radiation strength $I_0$ at the photobioreactor ensures that the radiation strength effectively present in the bioreactor lies above the requisite threshold value also in case of decreasing light transmission, thus assuring the reproducibility of the cultivation conditions and a constantly high yield of CoQ10 from the microorganisms. In the context of the present invention, it has been realized that depending on algae type an increase of radiation strength shall not occur too early or be too strong in order to avoid an undesirable damage of the phototrophic microorganisms. It was thus found in the course of the present invention that the adaptation and optimization of the surface radiation strength either requires a gradual increase of the surface radiation strength from an initial value to a final value which depends on the algae type or that a constant increased surface radiation strength that is carefully adapted to the existing conditions shall be chosen.

In addition to the induction of oxidative stress by trivalent iron according to the invention, the method can further comprise the additional step of adding oleate to the culture medium. This addition subsequently leads to an increased mitochondrial proliferation in the cells. Because CoQ10/QH2 is formed in membranes, and particularly in the inner mitochondrial membrane, the addition of oleate, which is an important component of the mitochondrial membrane, contributes to an increase of the concentration of CoQ10/QH2 in the cells through increased mitochondrial proliferation. Advantageously, 0.05 to 0.50 ml oleate per liter culture medium is added. In this context, a particularly significant increase of the CoQ10/QH2 yield is achieved, in particular, with oleate amounts of 0.15 to 0.30 mill, preferably by adding 0.25 ml/l oleate to the culture medium.

It is recommended that the culture medium be supplemented with the oleate between the 1st and 12th cultivation day. In particular, the addition is done between the 3rd and 6th cultivation day. Preferably, the oleate is added on the 5th cultivation day. These values can vary depending on the cultivated species.

EXAMPLES

The examples given below shall demonstrate the effects of the modification of various culture parameters on the CoQ10/CoQH2 formation in phototrophic microorganisms. The green algae *Chlorella kessleri*, the blue algae *Spirulina vulgaris*, *Spirulina fusiformis* and *Spirulina maxima* and yellow-green algae which belong to the division Chlorophyta are used as model organisms, which were "stressed" to achieve a reduced cultivation time of up to 3 days using the cultivation method according to the present invention.

For the basic cultivation of *Spirulina* Sp. *fusiformis/Ch. kessleri* and yellow-green algae in photobioreactors, the ASW medium according to Jones et al. is used (Jones, R. F.; Speer, H. L. and Kury, W. 1963: *Studies on the Growth of the Red Alga Porphyridium cruentum. Physiologia Plantarum* 16, 636-643), which is produced—in a modified manner—according to the following protocol:

| Component | Amount [$L^{-1}$] |
| --- | --- |
| NaCl | 27.0 g |
| $MgSO_4 \cdot 7H_2O$ | 6.60 g |
| $MgCl_2 \cdot 6H_2O$ | 5.60 g |
| $CaCl_2 \cdot 2H_2O$ | 1.50 g |
| $KNO_3$ | 1.00 g |
| $KH_2PO_4$ | 0.07 g |
| $NaHCO_3$ | 0.04 g |
| Tris-HCl-Buffer pH 7.6 | 20 mL |
| Micronutrient solution III | 1.00 mL |
| Ultrapure water | 989 mL |

The micronutrient solution III mentioned in the protocol contains the following components with concentrations as listed:

| COMPONENT | STOCK SOLUTION | AMOUNT [$L^{-1}$] |
| --- | --- | --- |
| $ZnSO_4 \cdot 7H_2O$ | 10.0 MG · 10.0 $ML^{-1}$ | 1.00 ML |
| $MnSO_4 \cdot 4H_2O$ | 10.0 MG · 10.0 $ML^{-1}$ | 2.00 ML |
| $H_3BO_3$ | 2.00 MG · 10.0 $ML^{-1}$ | 5.00 ML |
| $Co(NO_3)_2 \cdot 6H_2O$ | 2.00 MG · 10.0 $ML^{-1}$ | 5.00 ML |
| $Na_2MoO_4 \cdot 2H_2O$ | 2.00 MG · 10.0 $ML^{-1}$ | 5.00 ML |
| $CuSO_4 \cdot 5H_2O$ | 0.50 MG · 100 $ML^{-1}$ | 1.00 ML |
| $VE-H_2O$ | — | 881 ML |
| EDTA (Titriplex III) | — | 0.40 G |
| $FeSO_4 \cdot 7H_2O$ ($Fe^{2+}$) | — | 0.70 G |
| EDTA (Titriplex III) | — | 0.40 G |

Moreover, the following substances are added to the medium as organic carbon sources:

| | |
| --- | --- |
| Glucose | 3.00 g · $L^{-1}$ (1.7 · $10^{-2}$ mol · $L^{-1}$) |
| Glycerine | 1.53 g · $L^{-1}$ (1.7 · $10^{-2}$ mol · $L^{-1}$) |
| Saccharose | 8.70 g · $L^{-1}$ (1.7 · $10^{-2}$ mol · $L^{-1}$) |
| Fructose | 3.00 g · $L^{-1}$ (1.7 · $10^{-2}$ mol · $L^{-1}$) |
| and sodium acetate | 1.37 g · $L^{-1}$ (1.7 · $10^{-2}$ mol · $L^{-1}$). |

In particular, the medium mentioned above does not contain any meat extract. For the optimized cultivation of *Spirulina* Sp. *fusiformis/Ch. kessleri* and yellow-green algae in photobioreactors, the ASW medium according to Jones et al. (loc. cit.)—again in a modified manner—is used and produced according to the following protocol:

| Component | Amount [$L^{-1}$] |
| --- | --- |
| NaCl | 27.0 g |
| $MgSO_4 \cdot 7H_2O$ | 6.60 g |
| $MgCl_2 \cdot 6H_2O$ | 5.60 g |
| $CaCl_2 \cdot 2H_2O$ | 1.50 g |
| $KNO_3$ | 1.00 g |
| $KH_2PO_4$ | 0.07 g |
| $NaHCO_3$ | 0.04 g |
| Tris-HCl-buffer pH 7.6 | 20 mL |

-continued

| Component | Amount [L$^{-1}$] |
|---|---|
| Micronutrient solution III | 1.00 mL |
| Ultrapure water | 989 mL |

The micronutrient solution III mentioned in the protocol contains the following components with concentrations as listed:

| COMPONENT | STOCK SOLUTION | AMOUNT [L$^{-1}$] |
|---|---|---|
| ZnSO$_4$•7H$_2$O | 10.0 MG · 10.0 ML$^{-1}$ | 1.00 ML |
| MnSO$_4$•4H$_2$O | 10.0 MG · 10.0 ML$^{-1}$ | 2.00 ML |
| H$_3$BO$_3$ | 2.00 MG · 10.0 ML$^{-1}$ | 5.00 ML |
| Co(NO$_3$)$_2$•6H$_2$O | 2.00 MG · 10.0 ML$^{-1}$ | 5.00 ML |
| Na$_2$MoO$_4$•2H$_2$O | 2.00 MG · 10.0 ML$^{-1}$ | 5.00 ML |
| CuSO$_4$•5H$_2$O | 0.50 MG · 100 ML$^{-1}$ | 1.00 ML |
| VE-H$_2$O | — | 881 ML |
| EDTA (Titriplex III) | — | 0.40 G |
| Fe$_2$(SO$_4$)$_3$ 9H$_2$O (Fe$^{3+}$) | — | 0.70 G |
| EDTA (Titriplex III) | — | 0.40 G |

Here it is essential that with respect to the protocol solution there is a replacement of iron(II) by iron(III).

The following substances are added to the medium as organic carbon sources:

| | |
|---|---|
| Glucose | 3.00 g · L$^{-1}$ (1.7 · 10$^{-2}$ mol · L$^{-1}$) |
| Glycerine | 1.53 g · L$^{-1}$ (1.7 · 10$^{-2}$ mol · L$^{-1}$) |
| Saccharose | 8.70 g · L$^{-1}$ (1.7 · 10$^{-2}$ mol · L$^{-1}$) |
| Fructose | 3.00 g · L$^{-1}$ (1.7 · 10$^{-2}$ mol · L$^{-1}$) |
| and sodium acetate | 1.37 g · L$^{-1}$ (1.7 · 10$^{-2}$ mol · L$^{-1}$). |

The medium mentioned above also does not contain any meat extract.

Appropriate photobioreactors are any known reactors that are thermally sterilizable and that comprise appropriate means for controlling the cultivation parameters. Particularly useful photobioreactors for this task are the ones of the following types:

Labfors 4 Lux (Infors, Switzerland)
Medusa in 10 L and 25 L size (QVF, Germany)
Flat-Panel-Airlift-photobioreactor (Subitec GmbH, Germany)

Comparative Example 1

Reference Measurement of the CoQ10 and CoQH2 Content in Native Microorganisms

The reference measurement with *Spirulina* ex. *Spirulina vulgaris* resulted in a CoQ10 content of 4.1·µg/g and a CoQH2 content of 18.4 µg/g. Thus, the CoQH2 content was a factor 4.5 higher than the CoQ10 content.

The reference measurement with *Chlorella kessleri* resulted in a CoQ10 content of 2.5 to 3.2·µg/g and a CoQH2 content of 10.9 to µg/g, which corresponds to a QH2/Q10 ratio of 4.3 to 4.5.

Comparative Example 2

Adaption of the Surface Radiation Strength (OFBS) in the Basic Culture Medium

For the cultivation of representatives of the genus *Spirulina* ex. *Spirulina vulgaris*, a gradual increase of the surface radiation strength (OFBS) from initially 20 up to 120 µE·m$^{-2}$·s$^{-1}$ versus a constant OFBS of 40 µE·m$^{-2}$·s$^{-1}$ and 120 µE·m$^{-2}$·s$^{-1}$, respectively, was applied under standard cultivation conditions for 13 to 15 days. A constant OFBS of 120 µE·m$^{-2}$·s$^{-1}$ resulted in a CoQ10 content of 3·µg/g and was slightly poorer than a constant OFBS of 40 µE·m$^{-2}$·s$^{-1}$, which resulted in a CoQ10 content of 5.6·µg/g.

A gradual increase of the OFBS (20 to 120 µE·m$^{-2}$·s$^{-1}$) resulted in the highest CoQ10 yields (7.5 µg/g). Compared to the standard cultivation at 120 µE·m$^{-2}$·s$^{-1}$ (3·µg/g CoQ10), a productivity increase by a factor of 2.5 was achieved. Compared to the standard cultivation at 40 µE·m$^{-1}$·s$^{-1}$ (5.6 µg/g CoQ10), a productivity increase by a factor of 1.33 was achieved. Compared to the screening test (4.1·µg/g CoQ10), a productivity increase by a factor 1.8 was achieved.

For the cultivation of *Chlorella kessleri* an increase of the constant surface radiation strength (OFBS) up to 140 µE·m$^{-2}$·s$^{-1}$ as compared to the OFBS of 80 µE·m$^{-2}$·s$^{-1}$ and 100 µE·m$^{-1}$·s$^{-1}$ respectively, under standard cultivation conditions was adopted.

The OFBS at a constant 80 µE·m$^{-2}$·s$^{-1}$ resulted in a CoQ10 content of 5 µg/g and thus had a disadvantageous effect to the CoQ10 production in *Chlorella kessleri*. The OFBS at a constant 100 µE·m$^{-2}$·s$^{-1}$ resulted in a CoQ10 content of 6.5 µg/g, whereas the OFBS at a constant 140 µE·m$^{-2}$·s$^{-1}$ resulted in a CoQ10 content of 6.2·µg/g, thus meaning that similar yields of CoQ10 were obtained; the OFBS at a constant 120 µE·m$^{-2}$·s$^{-1}$ resulted in a CoQ10 content of 7.0·µg/g and therefore gave the highest yield of the CoQ10 production of *Chlorella kessleri*. Compared to the standard cultivation at 80 µE·m$^{-2}$·s$^{-1}$ (with 5·µg/g CoQ10), a productivity increase by a factor of 1.4 was achieved. Compared to the screening test (2.5 to 3.2·µg/g CoQ10), a productivity increase by a factor of 2.2 to 2.8 was achieved.

Example 1

Substitution of Fe$^{2+}$ by Fe$^{3+}$ without Optimized OFBS

In clear deviation from the recommended basic conditions for the cultivation of *Spirulina fusiformis, Spirulina maxima, Spirulina vulgaris* and also of *Chlorella kessleri*, the amount of added Fe$^{2+}$ was replaced by an identical amount of Fe$^{3+}$, with the addition being made via the micronutrient solution. Subsequently, the content of CoQ10/CoQH2 was determined.

In the group of Spirulinas the substitution of Fe(II) by Fe(III) provided for an increase of CoQ10 in the dry biomass (DBM) of about 50% from 4.1·µg/g CoQ10 to 6.2·µg/g CoQ10).

In the group of *Chlorella kessleri* the substitution of Fe(II) by Fe(III) provided for an increase of CoQ10 in the DBM of about 47 to 56% (from 2.5·µg/g and 3.2·µg/g CoQ10, respectively, to 3.6·µg/g and 4.9·µg/g CoQ10, respectively.

Comparable effects could not be achieved with representatives of red/brown algae.

Example 2

Substitution of Fe$^{2+}$ by Fe$^{3+}$ under Conditions of Organism-Specifically Adapted OFBS The procedure was analogous to that of example 1, but variable concentrations of Fe$^{3+}$ (between 0 mg·L$^{-1}$ and 6·mg·L$^{-1}$ Fe$^{3+}$) were added to the culture medium. In the case of *Spirulina*, preferably about 2.7·mg·L$^{-1}$ Fe$^{3+}$ and in the case of *Chlorella* preferably about 3.5·mg·L$^{-1}$ Fe$^{3+}$ were added.

This allowed to increase the production of CoQ10 in the dry biomass of *Spirulina fusiformis/Spirulina maxima* by a factor of 20, namely from 4.1·µg/g CoQ10 (without addition of Fe$^{3+}$) to 82 µg/g CoQ10 (with the addition of Fe$^{3+}$ and by applying a gradually increasing OFBS adapted to this organism from initially 20 to 120 µE·m$^{-2}$·s$^{-1}$) and to a QH2/Q10 ratio of 4.5.

In the case of *Spirulina vulgaris*, an improvement by a factor of 24 was achieved, namely, from 4.1·µg/g CoQ10 (without addition of Fe$^{3+}$) to 94 µg/g CoQ10 (with addition of Fe$^{3+}$ and by applying a gradually increasing OFBS adapted to this organism from initially 20 to 120 µE·m$^{-2}$·s$^{-1}$) and the QH2/Q10 ratio was improved by a factor of 4.5.

Moreover, the exponential growth phase was shortened and concomitantly the cultivation time under the basic conditions was shortened (10 to 13 days).

Moreover, an increase in production of CoQ10 in the dry biomass of *Chlorella kessleri* by a factor of 31.2 was achieved, namely, from 3.2·µg/g CoQ10 (without addition of Fe$^{3+}$) to 100 µg/g CoQ10 (with addition of Fe$^{3+}$ and by applying a constant OFBS adapted to this organism of 120 µE·m$^{-2}$·s$^{-1}$) and of QH2/Q10 by a factor 4.5.

In a further test series with *Chlorella kessleri*, an even larger improvement of 34.8 was obtained, namely from 2.5·µg/g CoQ10 (without addition of Fe$^{3+}$) to 87 µg/g CoQ10 (with addition of Fe$^{3+}$ and applying a constant OFBS adapted to this organism of 120 µE·m$^{-2}$·s$^{-1}$), and the QH2/Q10 ratio was improved by a factor of 4.38.

Example 3

Effect of the Addition of Fe$^{3+}$ on CoQ10 Production of Yellow-Green Algae

The procedure was analogous to that of example 2, but using yellow-green algae, with variable concentrations of Fe$^{3+}$ (between 0 mg·L$^{-1}$ and 6·mg·L$^{-1}$ Fe$^{3+}$), preferably about 3.5·mg·L$^{-1}$ Fe$^{3+}$ being added.

For yellow-green algae, using a constant OFBS adapted to these organisms of 120 µE·m$^{-2}$·s$^{-1}$ under "native conditions", i.e. without the addition of Fe$^{3+}$, a content of 15 µg/g CoQ10 was achieved, whereas with the addition of 3.5·mg·l$^{-1}$ Fe$^{3+}$ and again with a constant OFBS of 120 µE·m$^{-2}$·s$^{-1}$ a content of 75 µg/g CoQ10 was reached. This corresponds to an enhancement of the production of CoQ10 in the biomass of the yellow-green algae by a factor of 5.

In a further test series the improvement factor with yellow-green algae was 5.6, namely from 16 µg/g CoQ10 (native) to 89 µg/g CoQ10 (with Fe$^{3+}$ addition and a constant OFBS adapted to these organisms of 120 µE·m$^{-2}$·s$^{-1}$).

In both test series a QH2/Q10 ratio of about 4.5 was reached.

Example 4

Modification of the Fe$^{3+}$ Content under the Optimized Conditions

By the addition of Fe$^{3+}$ the specific concentration of iron (III) in the biomass (BM) could be increased as follows:
in the case of *Spirulina fusiformis* from 11 µg/gBM (initial content, "native") to a final content of 33 to 37 µg/gBM;
in the case of *Spirulina maxima* from 12 µg/gBM (initial content, "native") to a final content of 36 to 40 µg/gBM;
in the case of *Spirulina vulgaris* from 15 µg/gBM (initial content, "native") to a final content of 45 to 51 µg/gBM.

Similarly, the specific concentration of iron(III) in the biomass of *Chlorella kessleri* could be increased from 22 µg/gBM (initial content, "native") to a final content of 61 to 66 µg/gBM.

This corresponds to an increase of the Fe$^{3+}$ concentration—especially for availability in human diet—in blue algae (Spirulinas) by a factor of 3 to 3.5 and in green algae (*Chlorella*) and yellow-green algae by a factor of 2.8 to 3, respectively.

Concluding Remarks

The melting point of the molecules CoQ10 and CoQH2 is 49° C. according to literature. By applying the production methods described above, the corresponding molecules obtain a higher stability. In particular, a higher heat resistance of at least 80° C. and also a cold resistance of at least −24° C. was found.

This inherent stability improvement can be further improved by appropriate stabilizers (chemical/physical, e.g. mono-triglycerides of fatty acids, fatty alcohols and esters thereof).

Both the medium of the present invention and also the micronutrient solution and the carbon source do not contain any animal components and can, therefore, be used under vegetarian and/or kosher and/or halal specifications.

Moreover, starting with the methods mentioned described above, the following can be produced:
a) an oily extract, produced from the oxidative and the optional oleate process with green/blue and yellow-green algae by applying inter alia Fe$^{3+}$;
b) a dried algae product (wherein a drying step according to known technologies can be used in accordance with temperature, e.g. freeze drying, spray drying and fluidized-bed drying etc.); in this process, particles with sizes of up to 100 µm are dispersible (soluble) in water;
c) a lipoid extract of algae (also denoted as algae oil).

The products obtained with this method can be used in the following application ranges/products (also see further below):
Food supplements/nutritional supplements→in the form of tablets, capsules, powders with various particle sizes;
Admixtures in food/luxury foods of all types;
Anti-aging products such as repair kits, creams, sunscreens;
Natural cosmetics;
Skin cell regeneration;
Homeopathic base;
Animal food and agrarian applications.
a) Extraction from the algae using the methods of vapor extraction, CO$_2$-extraction, liquid gas extraction, optionally with solubilization by active ingredient complex, e.g. using poloxamer as solubilizer, recrystallization, filtration, chromatographic purification:
The extracts encompass CoQ10 and CoQH2 and CoQ10/QH2, respectively, optionally with active ingredient complex.
By adding reduction agents and oxidation agents (enzymatic and/or chemical/physical), respectively, the content of the extract can varied.
Applications are possible in the following ranges:
Food supplements/nutritional supplements
Pharmaceutical drugs, also as additive for infusions
Athlete nutrition/Tube feeding
Anti-aging
Food and luxury foods b) Combinations A combination with other products/product groups (vitamins, minerals, trace elements and further molecules from the Co/enzyme range) offers unforeseen possibilities and an efficacy increase resulting therefrom.

Application Examples

Cold Drinks or Juices

The dried algae product can be blended as botanical raw material into various drinks, with a quantity of 2 to 3 g algae being considered the usual daily dose.

Warm Drinks

The dried algae powder or the oily extract, but also the products from the extraction, are useful for warm drinks:

Tea leaves can be sprayed with the oily extract as is done with bergamot oil. No effects on tea aroma were found.

The algae powder, the oily extracts but also the extraction products can be admixed to the mass for making soluble tea, coffee and herbal teas.

Bread/Bakery Products/Long-Life Bakery Products

An important aspect lies in the fact that the inherent stability improvement achieved with or without stabilizers leads to "bakeability". Accordingly, the dried algae powder can be admixed to the dough mixtures for subsequent baking. It is also possible to use the oily extract, which has the advantage that there is no effect on color. The extraction products can also be used in dough mixtures, although it is subject to special law regulations.

For long-life bakery or for the application as admixture for extruder production it is appropriate to use the dried algae product.

Special or improved results were obtained by spraying on the oily extract or the extraction products dissolved in oil after the extrusion process.

"Moisture Food", a special category of food products obtained from extruder products, which is also used for animal food, can also be produced with the raw materials produced according to the invention.

Animal Food

The dried algae powder can be used for producing vegetarian animal food, which is becoming increasingly popular. The oily extracts as well as the extraction products can be used as further ingredients in food portions or in dry food for pets.

Repair Kits/Beauty Kits

The application in repair kits in the domains of anti-aging and skin/cell regeneration is also possible. With the admixture of dried algae powder the repair kits or beauty kits contain an additional care ingredient in the sense of the so called Thalasso-Therapy. It is known that algae have a salutary effect against cellulitis. Accordingly, the oily extract as well as the extraction products can be used as additives for products against cellulitis.

The invention claimed is:

1. A method for increasing the contents of ubiquinone (CoQ10) and ubiquinol (CoQH2) in phototrophic microorganisms being cultivated in a culture medium in a bioreactor under light irradiation, wherein the phototrophic microorganisms are selected from the group consisting of blue-green algae, and wherein the method comprises a step of inducing oxidative stress, wherein the induction of oxidative stress is effected by incubating the phototrophic microorganisms together with $Fe^{3+}$ in the culture medium, wherein the incubation is carried out with a content of $Fe^{3+}$ in the culture medium of about 1 mg/l to about 6 mg/l, and wherein the incubation is performed with a temporally increasing surface radiation strength from initially 20 $\mu E \cdot m^{-2} \cdot s^{-1}$ up to 120 $\mu E \cdot m^{-2} \cdot s^{-1}$.

2. The method according to claim 1, further comprising an addition of 0.05 to 0.50 ml of oleate per liter of the culture medium.

3. The method according to claim 1, wherein the blue-green algae are selected from the group consisting of *Spirulina vulgaris*, *Spirulina fusiformis* and *Spirulina maxima*.

* * * * *